United States Patent
Reichenbach

(10) Patent No.: US 10,222,313 B2
(45) Date of Patent: *Mar. 5, 2019

(54) METHOD AND APPARATUS FOR SORTING PARTICLES USING ASYMMETRICAL PARTICLE SHIFTING

(71) Applicant: Steven H. Reichenbach, Redwood City, CA (US)

(72) Inventor: Steven H. Reichenbach, Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/248,972

(22) Filed: Aug. 26, 2016

(65) Prior Publication Data

US 2016/0363523 A1  Dec. 15, 2016

Related U.S. Application Data

(63) Continuation of application No. 12/500,390, filed on Jul. 9, 2009, now Pat. No. 9,427,688.

(Continued)

(51) Int. Cl.
*B01D 43/00* (2006.01)
*G01N 15/10* (2006.01)
(Continued)

(52) U.S. Cl.
CPC ......... *G01N 15/1056* (2013.01); *B01D 43/00* (2013.01); *B01L 3/502715* (2013.01);
(Continued)

(58) Field of Classification Search
CPC .............. B01D 43/00; B01L 3/502753; B01L 2300/0681; B01L 2300/0864; B01L 3/502715; B01L 3/502761
See application file for complete search history.

(56) References Cited

U.S. PATENT DOCUMENTS

| | | |
|---|---|---|
| 2,715,860 A | 8/1955 | Walters |
| 3,899,427 A | 8/1975 | Connelly et al. |
| 4,102,780 A | 7/1978 | Sun et al. |
| 4,214,981 A | 7/1980 | Giddings |
| 4,250,026 A | 2/1981 | Giddings et al. |
| 4,523,682 A | 6/1985 | Barmatz et al. |
| 4,737,268 A | 4/1988 | Glddtnos |
| 4,842,738 A | 6/1989 | Greenspan |
| 4,894,146 A | 1/1990 | Giddlnqs |
| 5,039,426 A | 8/1991 | Giddinqs |

(Continued)

FOREIGN PATENT DOCUMENTS

| | | |
|---|---|---|
| JP | 2006-67926 A | 3/2006 |
| WO | WO 2004/037374 A2 | 5/2004 |
| WO | WO 2008/016414 A2 | 2/2008 |

OTHER PUBLICATIONS

Bargiel, J., "Commercialization of Lateral Displacement Array for Dewatering of Microalgae," Case Western Reserve University, pgs title paoes and pp. 1-53, May 2009.

(Continued)

*Primary Examiner* — Joseph C Rodriguez
(74) *Attorney, Agent, or Firm* — Brinks Gilson & Lione

(57) ABSTRACT

An apparatus and method disperse particles suspended in a fluid with an obstacle field in the flow path of the fluid. The particles may be dispersed after an interaction with obstacles in the obstacle field. The obstacle-particle interactions may result in an asymmetrical particle shift in which the particles are dispersed in an asymmetrical manner relative to the obstacle and the fluid flow. Obstacles are arranged to separate particles flowing through the device based on individual obstacles having properties that are asymmetrical and are oriented and aligned for the separation.

21 Claims, 8 Drawing Sheets

Related U.S. Application Data

(60) Provisional application No. 61/079,440, filed on Jul. 10, 2008.

(51) Int. Cl.
*B01L 3/00* (2006.01)
*G01N 15/00* (2006.01)

(52) U.S. Cl.
CPC ... *B01L 3/502746* (2013.01); *B01L 3/502753* (2013.01); *B01L 3/502761* (2013.01); *B01L 2200/0652* (2013.01); *B01L 2300/0681* (2013.01); *B01L 2300/0864* (2013.01); *B01L 2400/0487* (2013.01); *B01L 2400/086* (2013.01); *G01N 2015/0065* (2013.01); *G01N 2015/1006* (2013.01); *G01N 2015/1081* (2013.01)

(56) References Cited

U.S. PATENT DOCUMENTS

| | | | |
|---|---|---|---|
| 5,141,651 | A | 8/1992 | Giddinas |
| 5,193,688 | A | 3/1993 | Giddinas |
| 5,240,618 | A | 8/1993 | Caldwell et al. |
| 5,290,401 | A | 3/1994 | Savisalo et al. |
| 5,427,663 | A | 6/1995 | Austin et al. |
| 5,715,946 | A | 2/1998 | Reichenbach |
| 5,909,813 | A | 6/1999 | Stelzer |
| 6,727,451 | B1 | 4/2004 | Fuhr et al. |
| 6,860,956 | B2 | 3/2005 | Bao et al. |
| 7,150,812 | B2 | 12/2006 | Huanc et al. |
| 7,276,170 | B2 | 10/2007 | Oakey et al. |
| 7,318,902 | B2 | 1/2008 | Oakey et al. |
| 7,390,388 | B2 | 6/2008 | Childers et al. |
| 7,472,794 | B2 | 1/2009 | Oakey et al. |
| 7,735,652 | B2 | 6/2010 | Inglis et al. |
| 7,807,454 | B2 | 10/2010 | Oh et al. |
| 7,837,944 | B2 | 11/2010 | Auner et al. |
| 8,783,467 | B2 * | 7/2014 | Loutherback .... G01N 27/44791 209/143 |
| 9,174,222 | B2 * | 11/2015 | Huang .............. B01L 3/502746 |
| 9,212,977 | B2 * | 12/2015 | Tang ........................ G01N 1/34 |
| 9,427,688 | B2 * | 8/2016 | Reichenbach ......... B01D 43/00 |
| 2007/0026381 | A1 | 2/2007 | Huang et al. |
| 2007/0158243 | A1 | 7/2007 | Rem et al. |
| 2008/0023399 | A1 * | 1/2008 | Inglis ................ B01L 3/502753 210/649 |
| 2008/0135502 | A1 | 6/2008 | Pyo et al. |
| 2010/0059414 | A1 | 3/2010 | Sturm et al. |
| 2010/0301171 | A1 | 12/2010 | Wood |
| 2010/0304485 | A1 | 12/2010 | Karnik et al. |

OTHER PUBLICATIONS

Cummings E.B., Singh AK., "Dielectrophoresis in Microchips Containing Arrays of Insulating Posts: Theoretical and Experimental Results," Analytical Chemistry, vol. 75, No. 18, Sep. 15, 2003.

Dahlstrom, Ph.D., D.A., Bennett, B.S. Ch.E., R.C., Emmett, Jr., B.S., Ch.E., R.C., Harriott, Ph.D., P, Laros, M.S., T, Leung, Sc.D., W., McCleary, C., Miller, Ph.D., S.A., Morey, Ph.D., B, Oldshue, Ph.D., J.Y., Priday, B.S., Ch.E., G., Silverblatt, M.S., Ch.E., C.E., Skottee, M.S., Ch.E., J.S., Smith, B. Chem., Ch.E., J.C., Todd, Ph.D., D.B., "Liquid-Solid Operations and Equipment," The McGraw-Hill Companies, Inc. Section 18, pp. 18-1 to 18-134, 1999.

Davis, J. A. et al., Deterministic hydrodynamics: Taking blood apart, Proceedings of the National Academy of Science,www.pnas.org/cgi/doi/10.1073/pnas.0605967103, vol. 103, No. 40, pp. 14779-14784, Oct. 3, 2006.

Eijkel, J.C. et al., "Nanotechnology for membranes, filters and sieves," The Royal Society of Chemistry 2006, Lab Chip, 2006, 6, pp. 19-23, 2006.

EPO Search Report, EP 09 795 190.9, filed Jan. 25, 2011, dated Dec. 13, 2011.

Huang L.R, Tegenfeldt J.O., Sturm J.C., Austin R.H., Cox E., "A Microfabricated device for separating—200 kilo-base-pair dna molecules in—15 seconds," http://prism.princeton.edu/Sturm_publications/CP.193.MTAS.2002.pdf (Princeton Institute for the Science and Technology of Materials (PRISM), 2002.

Huang R., Barber T.A., Schmidt M.A, Tompkins R.G., Toner M., Bianchi D.W., Kapur R, Flejter W.L., "A microfluidics approach for the isolation of nucleated red blood cells (NRBCs) from the peripheral blood of pregnant women," Prenatal Diagnosis 2008: 28: 892-899.

Huang, L. R., "Continuous Particle Separation Through Deterministic Lateral Displacement," www.sciencemag.org, Science, vol. 304, pp. 987-990, May 14, 2004.

International Search Report and Written Opinion dated Feb. 3, 2010, PCT/US2009/050112, filed Jul. 9, 2009.

Keller et al., "Separation quality of a geometric ratchet," PhyRevE. 65.041927, published Apr. 11, 2002.

Mohan A., Doyle P.S., "Effect of disorder on DNA electrophoresis in a microfluidic array of obstacles," Physical Review E 76, 040903(R), 2007.

Morton K.J., Loutherback K., Inglis D.W., Tsui O.K., Sturm J.C., Chou S.Y., Austin R.H., "Hydrodynamic metamaterials: Microfabricated arrays to steer, refract, and focus streams of biomaterials." Proceedings of the National Academy of Science, vol. 105, No. 21, 7434-7438, May 27, 2008.

Nagrath S., Sequist L.V., Maheswaran S., Bell D.W., Irimia D., Ulkus L., Smith M.R, Kwak E.L., Digumarthy S., Muzikansky A, Ryan P., Balis U.J., Tompkins RG., Haber D.A., "Toner M. Isolation of rare circulating tumour cells in cancer patients by microchip technology Nature," vol. 450, 1235-1239, Dec. 20, 2007.

Perry, RH., Green, D.W., Ackers, D.E., Maloney, J.O., editors. "Perry's Chemical Engineers' Handbook 7th edition," McGraw-Hill New York, pp. 1-10, 1997.

Randall G.C., Doyle P.S., "Electrophoretic Collision of a DNA Molecule with an Insulating Post," Physical Review Letters, 93.058102, vol. 93, No. 5, 2004.

Tsutsui, H. et al., "Cell separation by non-inertial force fields in microfluidic systems," Mechanics Research Communications 36, pp. 92-103, 2009.

* cited by examiner

METHOD AND APPARATUS FOR SORTING PARTICLES USING ASYMMETRICAL PARTICLE SHIFTING

PRIORITY CLAIM

This application is a Continuation of U.S. application. Ser. No. 12/500,390, now U.S. Pat. No. 9,427,688, issued on Aug. 30, 2016, filed on Jul. 9, 2009, titled METHOD AND APPARATUS FOR SORTING PARTICLES USING ASYMMETRICAL PARTICLE SHIFTING, which claims priority to Provisional Patent Application 61/079,440, filed on Jul. 10, 2008, titled METHOD AND APPARATUS FOR SORTING PARTICLES SUSPENDED IN A FLUID USING ASYMMETRICAL PARTICLE SHIFTING, both of which are hereby incorporated by reference.

FIELD OF INVENTION

Dispersion may be used for sorting particles suspended in a fluid.

BACKGROUND

Various methods exist for concentrating particles in a fluid or separating particles from a fluid. In filtration, particles that are greater in size than the filter pore size are excluded or filtered out. Depth filters which do not have a specific pore size may trap particles in a filler matrix. Filtration is not easily implemented when the goal is to recover particles. In addition, filters may become clogged or caked which limits the usefulness of the filtration technique. Centrifugation is another method that may require the particles to have a different density or specific gravity than the fluid in which the particles are suspended. Adapting the centrifugation process for continuous processes may be complex and costly. Methods such as centrifugation, electrophoresis, and sedimentation may rely on unidirectional forces created by centripetal acceleration, electrostatic or electromagnetic fields, or gravity, respectively. These unidirectional forces may only allow particle migration in one direction. Chromatography is another method that relies on the selective retardation of some particles relative to the suspending flow. Some forms of industrial "scrubbers" separate particles by using elements that the particles stick or adhere to in order to trap the particles. For separating particles that have a higher density than the suspending fluid, inertial effects are often utilized, but such methods may require the suspending fluid to undergo an acceleration or change in flow direction. The particles, with their higher inertia do not always follow the flow and thus may be separated from the fluid. Some separation approaches used in micro fluidic systems configure flow paths or channels to influence the particle paths and exclude or direct particles away from some regions.

Obstacle based methods are other approaches that can be used in separation processes to circumvent the limitations of many of the other approaches for concentrating particles in a fluid or for separating particles from a fluid. For example, a field of obstacles may include surface coatings that bind to certain cell types. As a solution passes through the field in a micro-fluidic device, the specific cells bind to the obstacles and are immobilized, thus allowing the use of a fluoroscopic method to detect the cells of interest. Existing obstacle based separation techniques may use obstacles that shift obstacles in only one direction. Thus all particle-obstacle interactions result in a unidirectional shift relative to the fluid. Depth filters may utilize obstacles placed in a flow field to separate particles from a solution. When a solution initially enters a depth filter, the particles can pass though the filter, however, as the solution flows, the particles collect or deposit between the obstacles (e.g. fibers) either by adhesion or by jamming between the filter elements. Fibrous filters are another type of filter in which fibers are used for separation, which is achieved by the deposition of particles on collecting bodies.

It may be advantageous to separate particles in a process that is simple, efficient, and inexpensive and can be used in a continuous process that is less subject to clogging. It may be advantageous to collect particles suspended in a fluid instead of trapping or excluding them in a process that may be easily implemented in a broad variety of applications across a large range of processing scales.

BRIEF DESCRIPTION OF THE DRAWINGS

The system and method may be better understood with reference to the following drawings and description. Non-limiting and non-exhaustive embodiments are described with reference to the following drawings. The components in the drawings are not necessarily to scale, emphasis instead being placed upon illustrating the principles of the invention. In the drawings, like referenced numerals designate corresponding parts throughout the different views.

DETAILED DESCRIPTION

Figure 1:
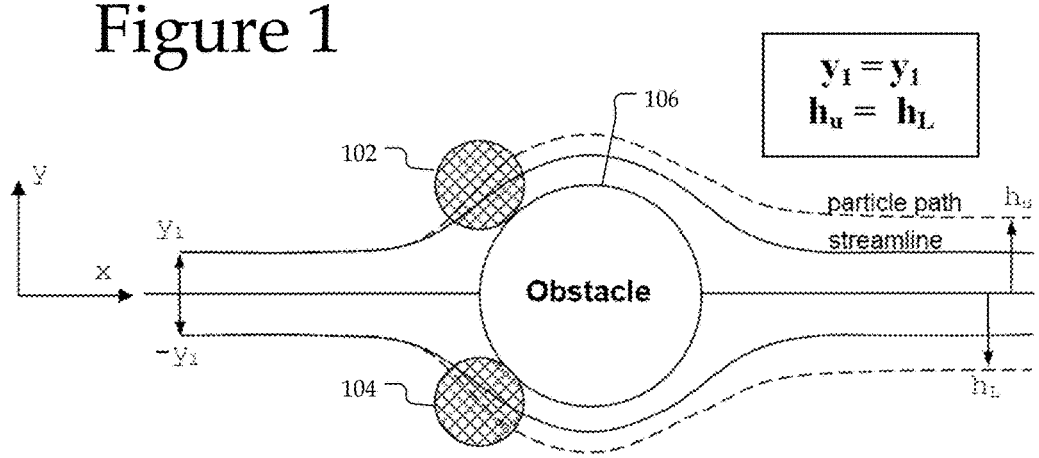
FIG. 1 illustrates a particle shift caused by an obstacle.

The present disclosure relates to a method and apparatus for sorting particles suspended in a fluid and, more specifically, to a method and apparatus that employ an asymmetrical obstacle induced preferential dispersion ("AOIPD") process using directionally non-uniform/asymmetrical interactions between the particles and obstacles. "Particles" may include materials such as cells, cellular fragments or components, cell aggregates, proteins and solid particles composed of various substances such as precipitates, crystal particles, or rock/sediment, for example. With appropriately scaled systems, the particles may be on the molecular scale. The term "fluid" may include both liquids and gases. As described, AOIPD may be used in the areas of biotechnology diagnostics and analysis, microfluidics, blood components processing, fermentation processes and recovery of cells in biotechnological processes.

Obstacle induced preferential dispersion ("OIPD") is an approach that can be used as a separation processes. OIPD may circumvent the limitations of other approaches for concentrating particles in a fluid or for separating particles from a fluid. OIPD is further described in U.S. Pat. No. 5,715,946, dated Feb. 10, 1998, issued to Steven H. Reichenbach, which is hereby incorporated by reference in its entirety. OIPD may rely on an interaction of particles with obstacles to cause a shift in the particle location in a direction perpendicular to the local flow. Although the particle-obstacle interactions can shift particles to either side of the obstacle, devices may be configured to create a preferential dispersion of the particles. Asymmetrical obstacle induced preferential dispersion ("AOIPD") may utilize obstacles in the solution flow path, but obstacles may be employed that shift particles perpendicular to the flow and in directions to either side of the obstacles. The resulting magnitude of shift may not be equal in both directions. In other words, the shift of the particle is asymmetrical with respect to the obstacle. OIPD utilizes obstacles in which the shift is generally symmetrical.

Obstacles utilized in AOIPD may create lateral particle shifts of different magnitudes depending on the side of the obstacle that the particle interacts with. The asymmetrical particle shift generated by the interaction with an obstacle creates different magnitudes of particle shift on each side of the obstacle. The asymmetrical shifts may result in a net migration or preferential dispersion of particles perpendicular to the flow direction. Even though the particles may be shifted to either side of the obstacle, it can be shown mathematically, as described below, that by appropriate orientation of such obstacles a preferential movement or separation of particle shifting may result from interactions with the obstacles. Accordingly, the AOIPD process does not require specialized obstacle placement or gradient creation.

AOIPD may create a higher flux rate of particles perpendicular to the suspension flow and it does not require particular obstacle placement or creation of high spatial gradients of obstacles. Further, AOIPD may be implemented with a uniform or random obstacle distribution. In addition, asymmetrical shifting by the obstacles can be configured to enhance the properties of the obstacle-particle interaction. In one embodiment, AOIPD may be implemented in a device along with OIPD and the migration of each can be implemented in opposite directions. Conversely, AOIPD may reinforce preferential dispersion of particles by OIPD because the asymmetrical shift includes an additional directional particle shift to OIPD. An obstacle's shifting properties in AOIPD may be aligned with other obstacles to control the preferential dispersion of particles after the asymmetrical shift.

According to a first aspect of the present disclosure, an apparatus preferentially disperses particles suspended in a fluid using an obstacle field. The properties of the obstacles used create an asymmetrical or non-uniform interaction between a particle and an individual obstacle. In other words, the interaction between an obstacle and a particle results in a particle shift of different magnitudes relative to the bulk fluid flow depending on the side of the obstacle with witch the particle interacts. The apparatus includes a conduit having one or more inlets, one or more outlets, and an inner lumen extending from the inlets to the outlets. A uniform or non-uniform obstacle field is disposed in the inner lumen. The obstacles are configured to preferentially disperse the objects suspended in the fluid as the fluid flows through the obstacle field. The preferential dispersion of the particles is caused by an asymmetrical interaction with the obstacles that results in an asymmetrical particle shifting.

According to a second aspect of the present disclosure, an apparatus disperses particles suspended in a fluid. The apparatus includes an inner lumen and an obstacle field disposed in at least a portion of the inner lumen. The obstacle field is configured to disperse, in a differential manner, the particles suspended in the fluid in a direction that deviates from local fluid flow. A re-circulating flow field allows at least a portion of the fluid flow to reenter the obstacle field.

According to a third aspect of the present disclosure, a method for preferentially dispersing particles suspended in a fluid includes providing a conduit having one or more inlets, one or more outlets and an inner lumen extending from the inlets to the outlets. A uniform or non-uniform obstacle field is located in a portion of the conduit. The properties of the obstacles used create asymmetrical or non-uniform interaction between the particles and obstacles. A fluid having particles suspended therein is injected through the conduit and the particles are collected at the output of the conduit.

According to a fourth aspect of the present disclosure, a method separates particles from a particle entrained fluid. The method includes directing the fluid to flow through a conduit having one or more inlets, one or more outlets, and an inner lumen extending from the inlets to the outlets. The particles are preferentially dispersed in a direction perpendicular to the direction of fluid flow through the conduit to create a particle depleted region at the outlet of the conduit. Alternatively, an external flow field may be utilized for the separation. The separation or concentration may be a local phenomenon that results in a region of the flow field where particles are depleted or concentrated.

Other systems, methods, features and advantages will be, or will become, apparent to one with skill in the art upon examination of the following figures and detailed description. It is intended that all such additional systems, methods, features and advantages be included within this description, be within the scope of the invention, and be protected by the following claims. Nothing in this section should be taken as a limitation on those claims. Further aspects and advantages are discussed below in conjunction with the embodiments.

FIG. 1 illustrates a particle shift caused by an obstacle. As a solution of particles passes through a group or field of obstacles the particles are shifted relative to the flow. Fluid flow in the region of an obstacle may be referred to as local fluid flow. The direction of the local fluid flow is along the x-axis. The first particle 102 and the second particle 104 encounter an obstacle 106. Both particles 102, 104 are displaced in a direction generally perpendicular to the flow of the suspending fluid. The particles 102, 104 are shifted resulting in a particle path different than the streamline. As shown, the cylindrical obstacle 106 has its longitudinal axis perpendicular to the direction of fluid flow. The first particle 102 is dispersed a distance of $h_u$ in the +y direction, and the second particle 104 is dispersed a distance $h_L$ in the −y direction. When $h_u$ equals $h_L$ the particle-obstacle interaction is symmetrical with respect to the fluid flow along the x-axis.

Figure 2:
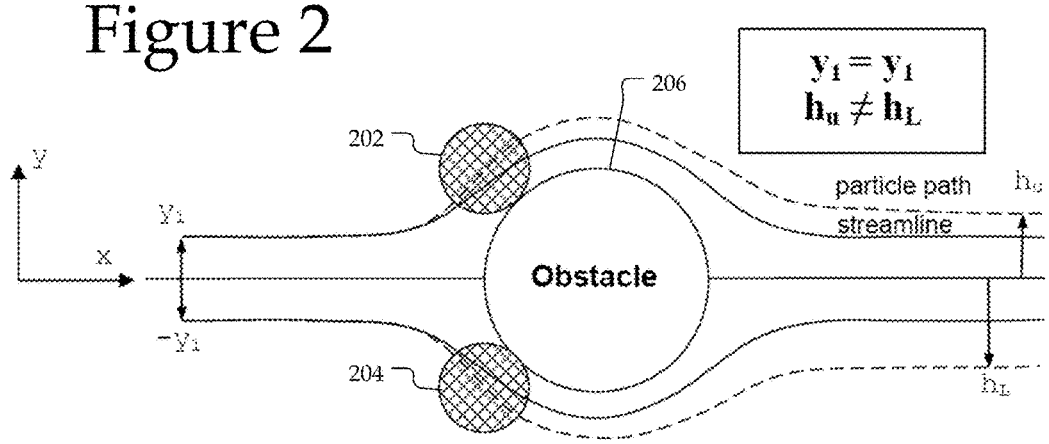
FIG. 2 illustrates an asymmetrical particle shift.

FIG. 2 illustrates an asymmetrical particle shift. The fluid flow is along the x-axis and includes a plurality of particles. As illustrated, a first particle 202 and a second particle 204 encounter an obstacle 206. The particles are displaced in a direction generally perpendicular to the flow of the suspending fluid at the obstacle 206. In an AOIPD apparatus, the shifting caused by the obstacle 206 is asymmetrical with respect to the fluid flow. The particle 202 encounters the obstacle 206 at a position of $+y_1$ and is shifted to a position of $h_u$. The particle 204 encounters the obstacle 206 at a position of $-y_1$ and is shifted to a position of $-h_L$. The asymmetrical interaction means that particles being displaced by the obstacle 206 are shifted asymmetrically relative the x-axis (fluid flow direction). The asymmetrical nature of the particle-obstacle interaction is illustrated in FIG. 2 by the fact that the magnitude of $h_u$ is different than the magnitude of $h_L$. The magnitudes of shift for each side of the obstacle are dependent upon several factors which will be described below in more detail.

Figure 3:
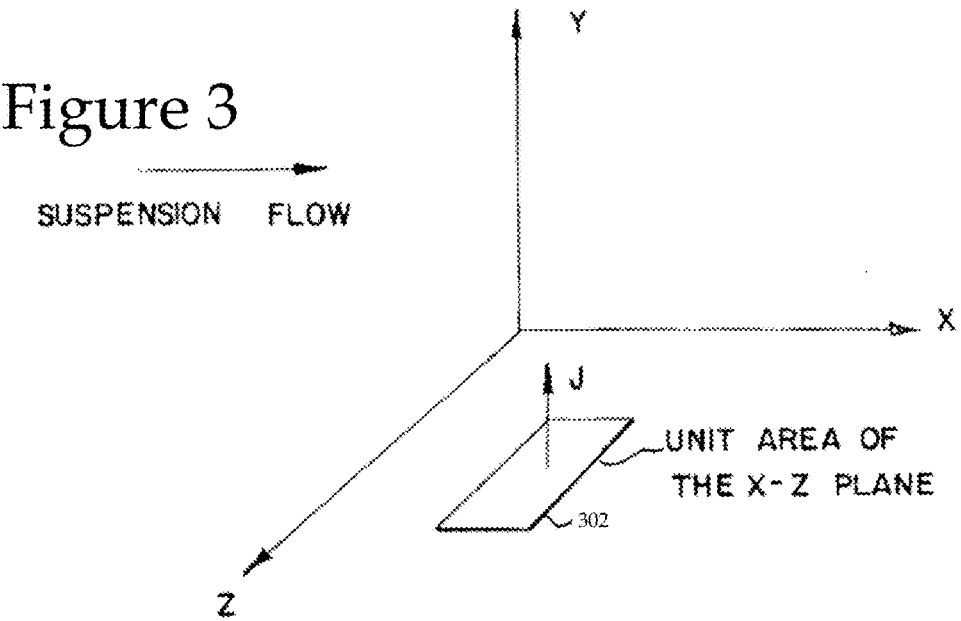
FIG. 3 illustrates a flux of particles through a surface normal to the flow.
Figure 4:
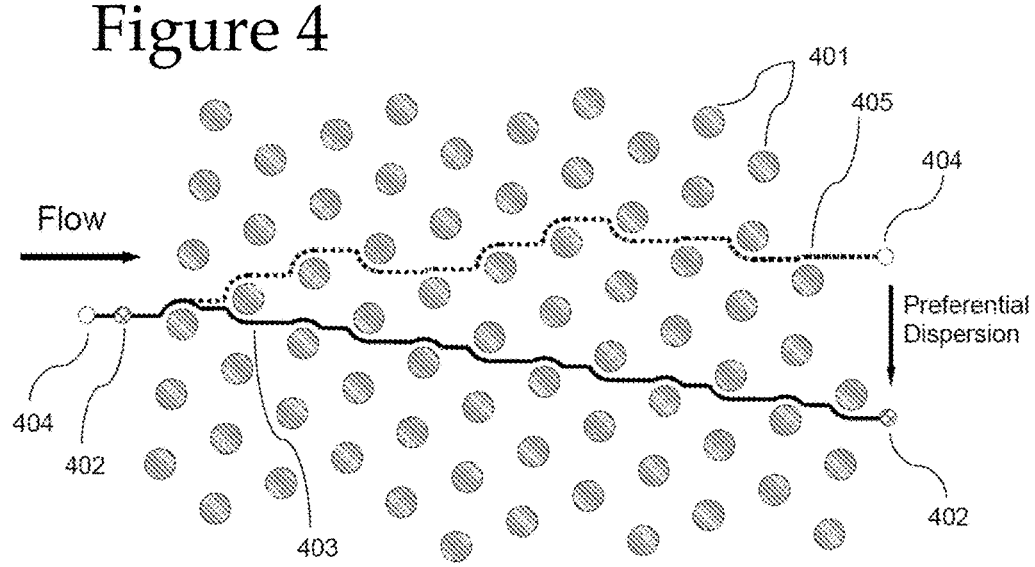
FIG. 4 illustrates migration of particles through an obstacle field.
Figure 5:
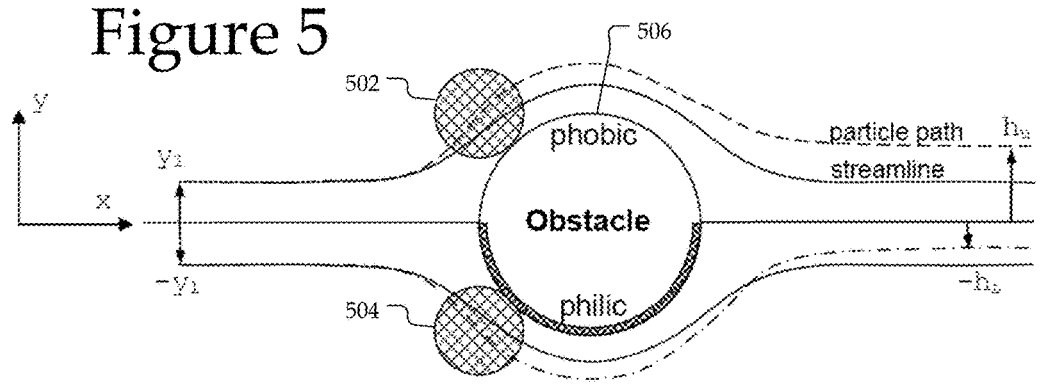
FIG. 5 illustrates an asymmetrical particle shift due to surface interaction.

FIG. 3 illustrates a flux of particles through a plane normal to the flow. An obstacle field can produce and enhance preferred dispersion of particles as described with respect to the flux of particles. A flux of particles, J, perpendicular to the fluid created by AOIPD can be described with respect to FIG. 3. In particular, particle flux is the rate at which particles pass through a surface per unit area of that surface. The particle flux in the Y direction is equal to the number of particles that pass through the unit area 302 per second.

Considering the particle flux, the theory upon which the obstacle field produces the preferred dispersion can be analyzed mathematically using a few assumptions. The assumptions merely help define the flux mathematically but the assumptions do not need to be present for AOIPD. First, it may be assumed that a dilute suspension of particles is present so that the movement of the particles does not influence the overall suspending fluid flow, and so that particles do not interact with one another. Second, it may be assumed that the obstacle field is also dilute so that a particle encounters only one obstacle at a time. It may further be assumed that there is fore and aft symmetry in the flow field around an obstacle and that particles follow the streamlines unless they interact with an obstacle. In addition, each particle that encounters an obstacle may be shifted perpendicular to the flow direction, to a position h (e.g. FIG. 2) from the obstacle centerline which is parallel to the flow direction.

With these assumptions in place the net particle flux J in the y direction for a suspension flow in the x direction can be described by equation (1) below:

$$J = \frac{h^2}{2}cu\chi(1-\alpha^2) + \frac{-h^3}{6}\left(2cu\frac{\partial\chi}{\partial y} + c\chi\frac{\partial u}{\partial y} + u\chi\frac{\partial c}{\partial y}\right)(1+\alpha^3) + O(h^4), \quad (1)$$

where c is the particle concentration, u is the velocity of the suspension, and $\chi$ is the concentration of obstacles. Particle flux may lead to particle separation in the AOIPD process. As defined above, the flux is dependent upon the asymmetry of the particle shift, $\alpha$, and the shift magnitude term, h, so by altering either parameter the AOIPD separation may be enhanced. These parameters may be influenced by both the obstacle and particle characteristics, and devices can be designed to tailor the process and allow selective separation or stratification of particles. As can be seen, the flux is also dependent on the gradients (spatial derivatives of obstacle concentration, particle concentration, and suspending fluid velocity). As described above, AOIPD driven flux is dependent not only by the gradient terms, but also directly by asymmetrical particle shift. Furthermore, because h may be small relative to other terms, the effect of the asymmetrical shift may be an order of magnitude larger than the gradient terms. Accordingly, AOIPD may provide a more efficient means of separation.

A particle may encounter an obstacle if upstream of the obstacle it is within the distance h of the obstacle centerline. Accordingly, if an obstacle is located between y=0 and $y=h_u$ upstream of the obstacle, it will be shifted to $y=h_u$ downstream of the obstacle. Any particle located between y=0 and $y=-h_L$ upstream of the obstacle will be shifted to $y=-h_L$. The variable describing the asymmetry of the shift, $\alpha$, is defined as the ratio of $h_u$ to $h_L$. As described by equation 1, the asymmetry of the particle shift, $\alpha$, may have a strong influence on the flux. Many factors may affect the magnitude of asymmetrical particle shift resulting from the interaction with a single obstacle. These factors may include particle size and shape; obstacle size, orientation and shape; distribution of obstacle surface properties and relative particle properties; charge distribution on the obstacle and on the particle; and the Reynolds number associated with the suspension flow over the obstacle. Obstacles with circular cross-sections, i.e. cylinders, are used in the present description for exemplary purposes only; however, obstacles having non-circular cross-sections may also be used and may be advantageous for particular applications. While the mathematical analysis assumed that the AOIPD process was performed using dilute suspensions, the process may also be effective at high particle concentrations.

FIG. 4 illustrates migration of particles through an obstacle field. The obstacle field includes obstacles that produce asymmetrical particle shifting with selected particles. In particular, FIG. 4 illustrates a process by which asymmetrical particle shifting results in a net migration of a particle 402 that has asymmetrical interactions with obstacles 401, in the obstacle field. A path 403 for the particle 402 is illustrated through the obstacle field. The particle 402 is carried by flow in the direction of the x-axis through a field of obstacles 401 whose properties may result in an asymmetrical shifting of the particle 402. The individual obstacles 401 may be oriented so that the asymmetrical shifts are aligned in the same direction. When a particle encounters an obstacle it is shifted in either in the positive y (+y) or negative y (−y) direction relative to the flow. Due to the asymmetrical shifting, if the particle is on the +y side of the obstacle, then the shift is smaller than the magnitude of shift resulting when the particle interacts with the −y side of the particle. Even though the particle may interact with both the +y and −y side of obstacles, the larger magnitude shift on the −y sides results in a net migration of the particle in the −y direction as the particle traverses the obstacle field.

FIG. 4 also illustrates the dispersion of a particle 404 that has symmetrical interactions within the same obstacle field. The second particle path 405 is that of the particle 404 having properties that result in symmetrical interactions with obstacles 401 in the field. Again the particles can be shifted in +y or −y direction, but the magnitude of shifts is equal regardless of the side of the obstacle 401 on which the interaction takes place. Due the symmetrical shifting, the particle 404 is dispersed by the shifts, but there may not be a net migration or preferential dispersion as with AOIPD. The fluid moves through stationary obstacles, or through obstacles that move relative to the lumen walls.

FIG. 5 illustrates an asymmetrical particle shift due to surface interaction. The surface property distribution on obstacle 506 may influence the downstream shift of particles 502, 504. One side of the obstacle 506 is philic, i.e.

attracting, which attracts the particle 504 and the particle 504 may tend to cling to the obstacle 506. The particle 504 may roll or slide along the back side of the obstacle 506, and "detach" closer to the obstacle centerline thus resulting in a smaller downstream particle shift than the phobic or neutral side of the obstacle 506. On the phobic or neutral side of the obstacle 506, the particle 502 is not attracted to the obstacle 506, so the particle path is different than the particle 504.

The asymmetrical shifting properties of the obstacles may be created in a number of ways. Asymmetrical surface properties may be created with a variety of coating or treatment methods on the obstacles. Directional sputter, spray coating, or deposition can be used to achieve the asymmetrical surface properties on an obstacle by partially coating each obstacle. Similarly, asymmetrical masking prior to coating may be employed. Directional etching techniques including optical treatments may also be utilized. Controlled recession of a coating fluid surface in a coating bath type process could also be used to provide the asymmetrical coating. Other methods can be used to partially coat or treat obstacles to provide the asymmetrical particle shifts.

The particle philic or phobic nature of the surface may be a result of material properties depending on the specific particles being shifted. Hydrophilic or hydrophobic surfaces may be employed for this purpose and can be a function of the base material or surface treatments, such as plasma etching. Such material properties and processing have been developed in the field of membrane separation. Antibody, antigen, and protein binding are other properties that can be leveraged in this application. Other properties may be known from cellular biology, genetics and the biotechnology industry.

Figure 6:
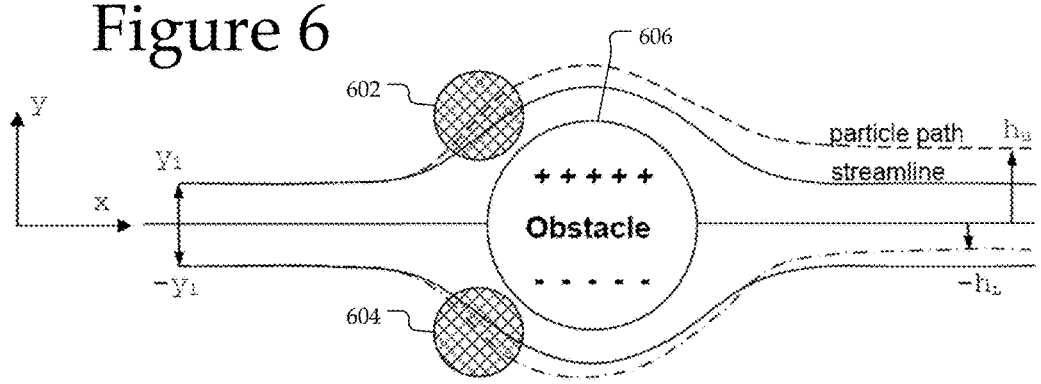
FIG. 6 illustrates an asymmetrical particle shift due to charge.

FIG. 6 illustrates an asymmetrical particle shift due to charge. An obstacle 606 may have a different charge on either side. In one example, the charge in the +y direction is opposite the charge in the -y direction of the obstacle 606. When the particles 602, 604 carry an electric charge and the obstacle 606 has a dipolar charge distribution, then particles on one side would be repelled and those on the other side would be attracted. In other words, the particle 602 may be repelled by the obstacle 606 and the particle 604 may be attracted to the obstacle 606 based on the charge distribution of the obstacle 606. The repelling and attracting of particles results in an asymmetrical shift of the particles at the obstacle 606. Oppositely charged particles would have an opposite asymmetrical shift and neutral particles would not shifted by the charge effects. Similarly, magnetized obstacles with the magnetic field properly oriented may also be used to provide an asymmetrical shift by either repelling or attracting particles depending on the side/orientation of the obstacle.

The charged obstacles may be created by constructing the charge properties or materials directly into fibers/obstacles. The surface charge properties of the obstacle maybe created after fabrication of the obstacles either by treatments that change the chemical properties of the surface or by application of charge. Microfluid device construction techniques may also be available for controlling surface charges. Active electrical approaches for creating asymmetrical charge may also be possible with some configurations. This active approach may include direct application of electrical potential to localized regions of the obstacles via electronic circuitry. Conductive or partially conductive particles may also be employed to create asymmetrical charges on the obstacles. Finally, conductive obstacles within an overall potential field gradient across the obstacles may cause charge on particles to migrate to opposite sides of the obstacles and thus form obstacles with asymmetrical charge properties.

Magnetization may also create asymmetrical particle shifts. Obstacles created from magnetic materials may be used to create fields with the desired directional particle shift properties. Materials that can be magnetized with the application of a strong external magnetic field may be used to fabricate an obstacle field with the desired shift properties after the field is assembled. The "un-magnetized" material may be assembled into the obstacle configuration, then a strong external field is applied to magnetize the obstacles with the desired magnetic field direction. As with surface charge, active approaches may be used to create the desired asymmetrical properties of the obstacles through the use of electromagnetic circuitry within the obstacles.

Figure 7:
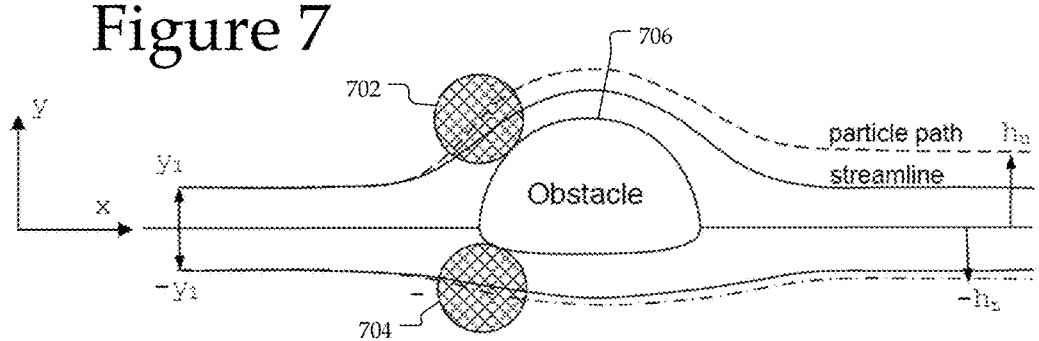
FIG. 7 illustrates an asymmetrical particle shift due to obstacle geometry.
Figure 8A:
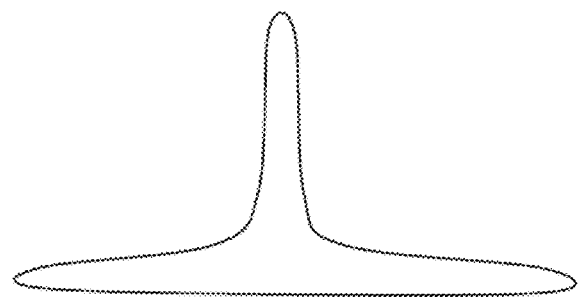
FIGS. 8a-8f illustrate exemplary obstacle geometries.
Figure 8B:
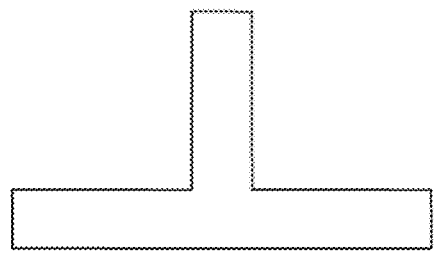
Figure 8C:
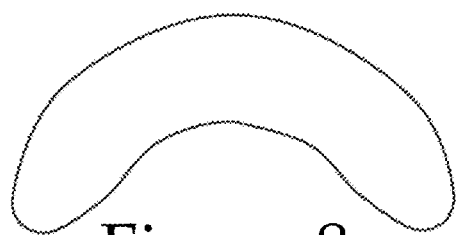
Figure 8D:
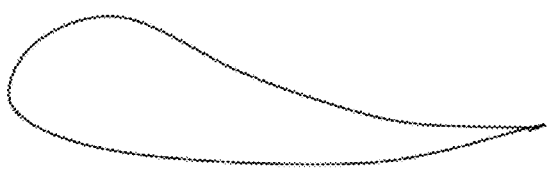
Figure 8E:
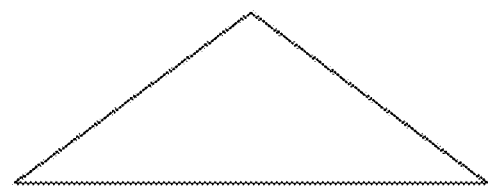
Figure 8F:
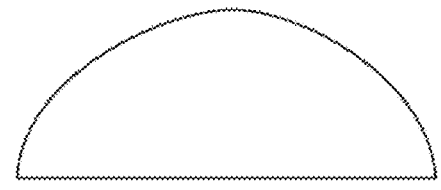

FIG. 7 illustrates an asymmetrical particle shift due to obstacle geometry. The geometry of the obstacle 706 and corresponding local flow patterns can also result in an asymmetrical particle shift. As shown, the shape of the obstacle 706 results in a smaller shift for particle 704 and a greater shift for particle 702. Geometrical features of the obstacle may create a flow field that brings more streamlines closer to the surface and result in more particle interactions. A packing of streamlines may allow the obstacle interaction with the particles to shift particles across more streamlines which correspond with a larger downstream particle shift h. Such local flow effects may result in asymmetrical particle shifts. A wide variety of obstacle shapes may be used to produce asymmetrical shifts as shown in FIGS. 8a-8f. The obstacle shape may be further optimized depending on the flow conditions, particle characteristics, and/or other obstacle characteristics.

Application of obstacle geometry or shape may be realized in a variety of ways. Obstacles extruded with the desired shape may be assembled with the uniform orientation to create the AOIPD field. Micro-fluidic, MEMS, nanotechnology or other fabrication techniques may also be used to create the obstacles in place having the desired shape and orientation. Micro post arrays may be incorporated in microfluidic devices such as lab-on-a-chip type devices used in chemical and biological analysis. Obstacles with asymmetrical properties may also be created with post-assembly approaches that distort or etch the obstacles to the desired configurations.

Particular embodiments of devices that may be used to implement the AOIPD process will now be described. By providing non-uniform obstacle-particle interactions, the net shift in path of the particles may be controlled and directed in a specific direction. By orientating the obstacles such that the asymmetrical shifts are aligned in the same direction as the gradient driven particle flux, the AOIPD process may be more efficient for executing the separation process. Alternatively, the asymmetrical shift may be used to drive the particles in an opposite direction as the gradient based dispersion. By doing so, particles that are subject to the asymmetrical shift may be driven in one direction while particles with properties that result in a symmetrical shift may be shifted in the opposite direction. This will allow more selective separation or stratification of particle mixtures that is dependent on the individual particle properties.

Figure 9:
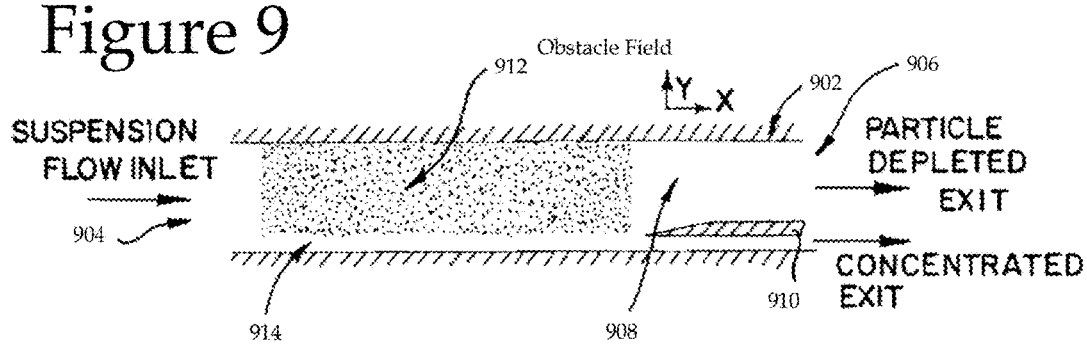
FIG. 9 illustrates a cross-sectional view of an apparatus for AOIPD along the suspension flow direction.

FIG. 9 illustrates a cross-sectional view of an apparatus for AOIPD along the suspension flow direction. The apparatus includes a conduit or a duct 902. In an alternative embodiment, the duct 904 may be a receptacle through which a fluid is passed from a first region to a second region. The duct 902 may have a cross section that is rectangular in shape. The duct 902 has an inlet 904 and an outlet 906 and an inner lumen 908 extending from the inlet to the outlet. The inlet 904 is coupled to a source of fluid having particles suspended therein (not shown). A splitter plate or wall 910 near the outlet 906 of the duct 902 divides the outlet into two outlets so that the concentrated particles and the particle depleted solution can be separately collected. An obstacle field 912 is located in the interior of the duct 902 between the inlet 904 and outlet 906 of the duct. In an alternative embodiment, the inlet 904 may be referred to as a first region and the outlet 906 may be referred to as a second region. The fluid may be dispersed from the first region to the second region. For example, in a microfluidic device, such as a chip, the fluid may pass from a first region to a second region and the obstacle field 912 may be present along the path of the fluid from the first region to the second region. The obstacle field 912 may be formed by or comprise a collection of posts separated sufficiently to avoid trapping particles. The obstacles are orientated or treated to produce asymmetrical particle shifts with the larger magnitude shifts for all obstacles orientated toward obstacle free region of the duct. The obstacle field 912 may be uniform on one side of the duct 902 and may be absent on the other side, thereby creating a step in the spatial density across the duct 902 or a non-uniform obstacle field. The depth of the obstacle free region 914 of the duct may be kept relatively small to keep the flow velocity more uniform across the duct. The obstacle free region may not be necessary, but illustrates one embodiment that may reinforce the AOIPD separation process with a spatial obstacle gradient. The dimensions of such devices may be dependent on the application of use. For bulk separation, the size of the device may be dependent on the particle size and the volume to be processes. This size may cover orders of magnitude in the application from microfluidics to industrial process feed streams.

The obstacle field may be implemented in a number of ways. Current techniques for micro-fluidic device construction may allow creation of obstacle fields or post arrays within the devices. These techniques may allow great flexibility in tailoring the fields as well as the obstacle properties. Other approaches may also be used. For example, the obstacle field may be created from a random collection of fibers, or a series of screen or mesh material, coiled or folded mesh, individually placed fibers or rods and possibly a porous material having interconnecting compartments large enough for the particles to pass through without being trapped. A variety of methods may be used to secure the obstacle field within the conduit. In one embodiment, friction may be used for force fitting of the obstacle matrix in the conduit. Adhesives may also be employed to secure the obstacle field in place. The obstacles may be "potted" within the duct wall itself, in which the edges of the obstacles or obstacle matrix are embedded in a liquid wall material such as polyurethane, and once in place, the wall material is allowed to cure. Alternatively, when the obstacle fields include a series of meshes placed perpendicular to the flow, each mesh is sandwiched between thin washer-like sections of the duct wall.

The obstacles within the field may be oriented such the asymmetric particle shift is aligned in the desired direction. If the asymmetrical shift contribution is to be combined with the gradient driven dispersion (see Equation 1), then the larger particle shift side of the obstacles may be oriented in the same direction as the gradient driven flux. If the process is to be used to selectively separate particles that are subjected to the asymmetrical shift, then the direction of the asymmetrical shift may be reversed, thus forcing particles dominated by the asymmetrical shift magnitude in one direction and other particles shifted in the opposite direction by the gradient driven dispersion.

Local modification of global field effects due to obstacle properties may create asymmetrical particle shifts. For example, ferrous material in a magnetic field may create directional local fields around the obstacles that create asymmetrical particle shifts. Conductive obstacles placed in an electrical field may also create local asymmetrical field around the obstacles resulting in asymmetrical particle shifts. Other field effects might also be manipulated to create asymmetrical shifts such as the local focusing of an acoustic field.

Figure 10:
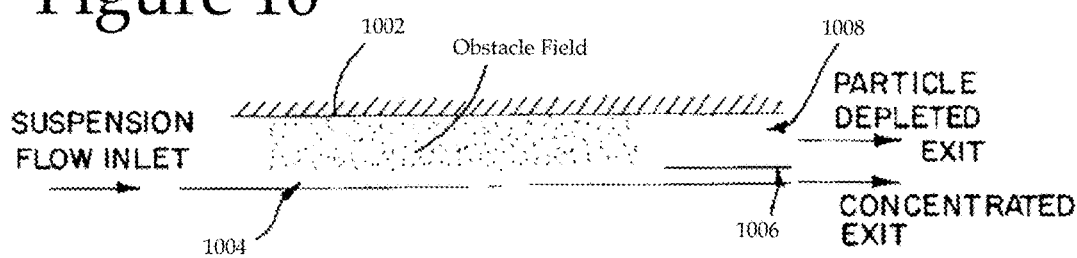
FIG. 10 illustrates a cross-sectional view of an alternative axially symmetric apparatus for AOIPD.

FIG. 10 illustrates a cross-sectional view of an alternative apparatus for AOIPD. Instead of a rectangular duct as shown in FIG. 9, a non-rectangular or axial symmetrical geometry may be used as illustrated in FIG. 10. The apparatus has an axially symmetric configuration in which the center of the cylinder is obstacle free. As shown, one half of the cylinder 1002 is illustrated, with the center axis of the duct indicated by dashed line 1004. A second cylinder 1006 at the outlet 1008 divides the outlet 1008 in two. The second cylinder 1006 has a smaller diameter than cylinder 1002 and is concentrically positioned with respect to cylinder 1002. The center cylinder 1006 collects the concentration of particle while the particle depleted fluid flows through the annular region between the outer cylinder 1002 and the inner cylinder 1006. The obstacles within the field may be oriented such the asymmetric particle shift is directed in the desired directions.

Figure 11:
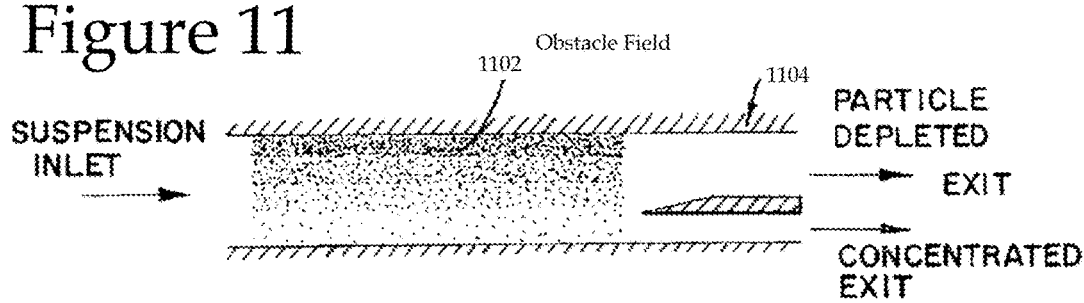
FIG. 11 illustrates a cross-sectional view of an alternative apparatus for AOIPD.

FIG. 11 illustrates a cross-sectional view of an alternative apparatus for AOIPD. The obstacle field 1102 is similar to that previously described with reference to FIG. 9; however, the obstacle field 1102 may be created by parallel posts that traverse the duct 1104. The characteristics and spatial density of the obstacle field 1102 may be selected depending on suspension and particles of interest. As with the other embodiments, the obstacles within the field may be oriented such the asymmetric particle shift is directed in the desired direction. In this embodiment there is no obstacle free region. While the apparatus shown in FIG. 11 incorporates a rectangular duct, it may also be implemented in an axially symmetrical configuration.

The apparatus used to carry out the AOIPD method results in preferential dispersion of particles by passing a fluid containing the particles through a field of obstacles that induce dispersion of the particles in a direction generally perpendicular to the fluid flow. By properly configuring the obstacles, the dispersion may be produced in a particular direction, i.e. the particles migrate in one direction. This preferential dispersion may result in a non-uniform concentration of particles downstream of the obstacle field. By appropriate collection, a solution with increased or decreased particle concentration may be obtained. The rate of migration of the particles may also be dependent upon particle size or characteristics. By providing various collection points along the fluid flow path, particles of different sizes or characteristics may be extracted from the fluid at different points along the conduit. In an alternative embodiment, a spacer may be utilized to maintain more uniform flow through the obstacle field. The shape of the AOIPD device may be used to control flow velocity gradients, as well as spacers (e.g. surfaces to slow the flow) in the regions with lower obstacle concentration. U.S. Pat. No. 5,715,946 further illustrates the use of a spacer.

AOIPD may be incorporated into micro-fluidic devices using a variety of different configurations. Because many such devices perform various processing or analysis steps within the device, explicit collection of particles may not be necessary. Separated particles or solute may be directed to specific regions of the device for processing or analysis. The collection sections and conduits may not be explicitly defined, but the principles are the same. Micro-fluidic devices may also utilize recirculation of the flow through an obstacle region to reduce the physical length of the obstacle region used. The recirculation may be created using shear driven force or more direct pumping methods.

Figure 12:
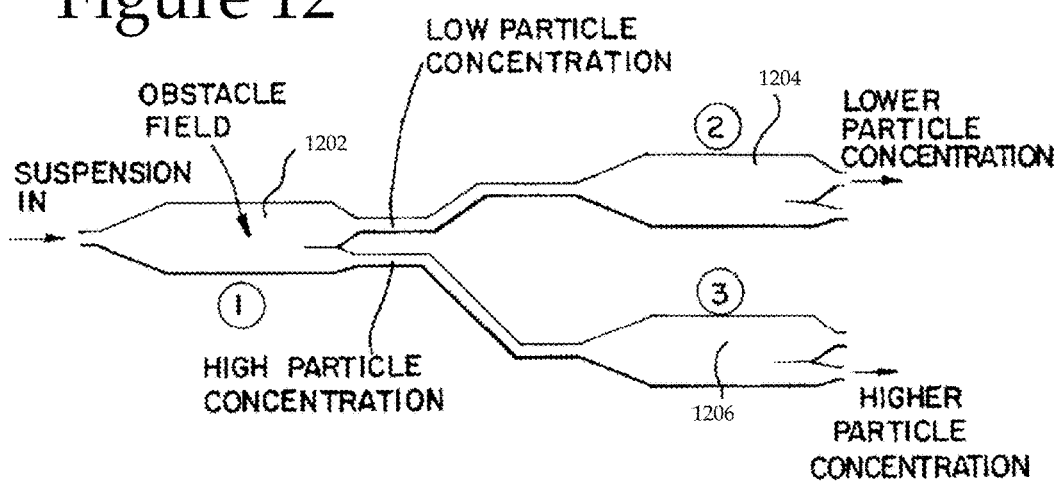
FIG. 12 illustrates a cross-sectional view of multiple cascaded devices.

FIG. 12 illustrates a cross-sectional view of multiple cascaded devices. Multiple cascaded devices may be used to achieve desired particle depleted and particle rich suspension concentrations. Such a cascaded arrangement may enhance the particle concentrating/depleting effects. A similar arrangement could be used to separate or stratify a solution containing particles with different characteristics. In order to stratify a solution with multiple particle sizes, the obstacle fields 1202, 1204, and 1206 may have different characteristics, for example, the size of the obstacles in each field may be different, or they may be charged differently. These devices may not exclude particles since using a diffusion process does not guarantee a solution void of particle. A small concentration may be left. In addition, a series of devices with different characteristics (obstacle surface properties etc.) may be useful for separation of suspensions containing multiple particle types. For example, a series of devices could be designed to successively remove particular particles in the solution.

Figure 13:
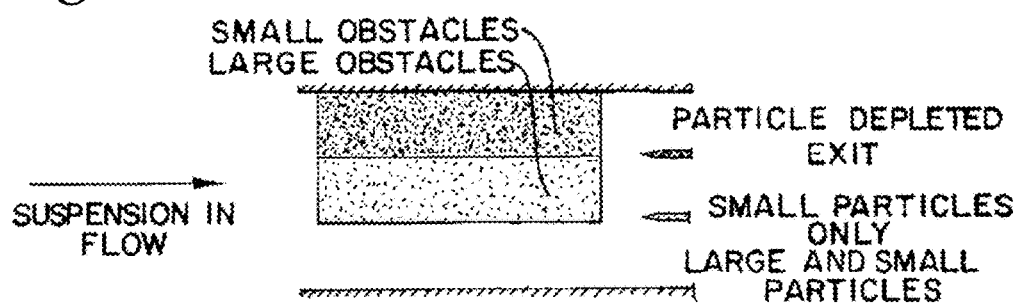
FIG. 13 illustrates a cross-sectional view of an apparatus used to stratify particles of different sizes.

A cascaded arrangement may not be required for stratifying multiple particle types. Because the asymmetrical particle shift is dependent on the particle and obstacle characteristics, a device with several fields containing different obstacle characteristics may stratify a mixture of particle types. A configuration is shown in FIG. 13. For exemplary purposes, a suspension of small and large particles may be considered. Large obstacles may shift the larger particles, but may not have much effect on smaller particles. The particle flux normal to the flow direction is a function of h, so larger obstacles would produce virtually no flux of smaller particles. The smaller obstacles in FIG. 13 would be able to shift the smaller particles and drive the separation of both the small and large particles. Similarly, stratification of differently charged particles or particles with different surface properties may be achieved with regions of obstacles having different properties.

Figure 14:
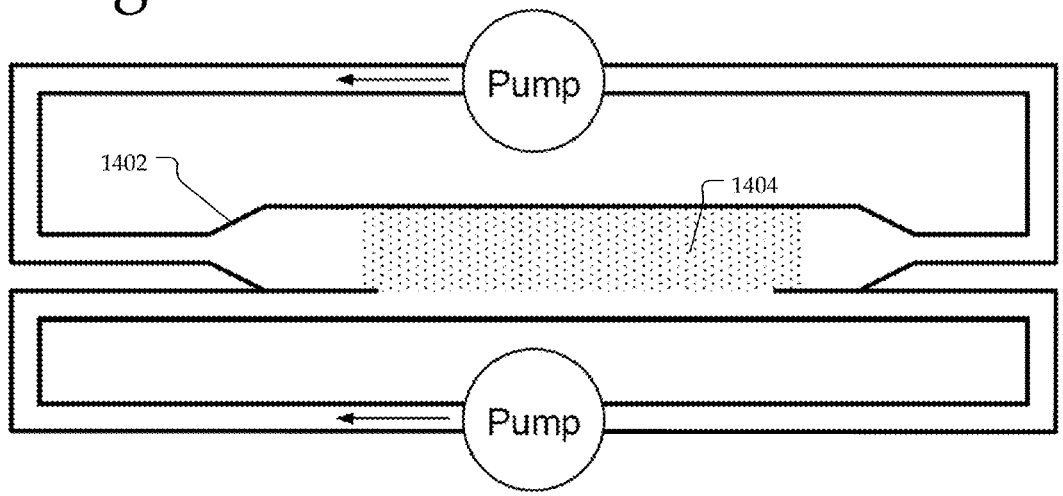
FIG. 14 illustrates a recirculating solution in an AOIPD device.
Figure 15:
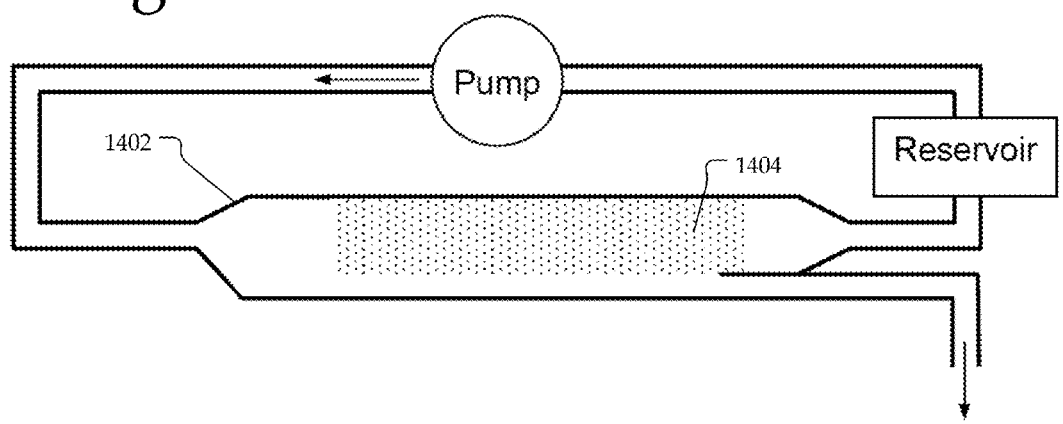
FIG. 15 illustrates a recirculating solution through an AOIPD device with a reservoir.

In order to achieve the final particle concentrations desired from the separation process, the length of the obstacle field in the direction of flow may need to be of sufficient length. To reduce this obstacle field length and still achieve the desired separation, the solution being processed can be re-circulated. Such recirculation may be implemented in a batch or continuous manner and can use single-stage type devices such as shown schematically in FIG. 14 or specially designed devices with re-circulating flow fields. As shown, a fluid flow at the chamber entrance 1402 passes through an obstacle field 1404. The chamber may also be referred to as the inner lumen. The fluid is re-circulated through the chamber. The direction of fluid flow may be the local flow at each obstacle of fluid passing through the obstacle field. To re-circulate with single-stage devices, the solution exiting the device is returned to the beginning of the same device to continue the separation process. With devices such as those illustrated in FIG. 14, the effluent form the device is returned to the entrance off the device either by a pumping or valving system as shown in FIGS. 14 and 15. In particular, FIG. 14 illustrates a recirculating solution through an AOIPD device, and FIG. 15 illustrates a recirculating solution through an AOIPD device with a reservoir.

Figure 16:
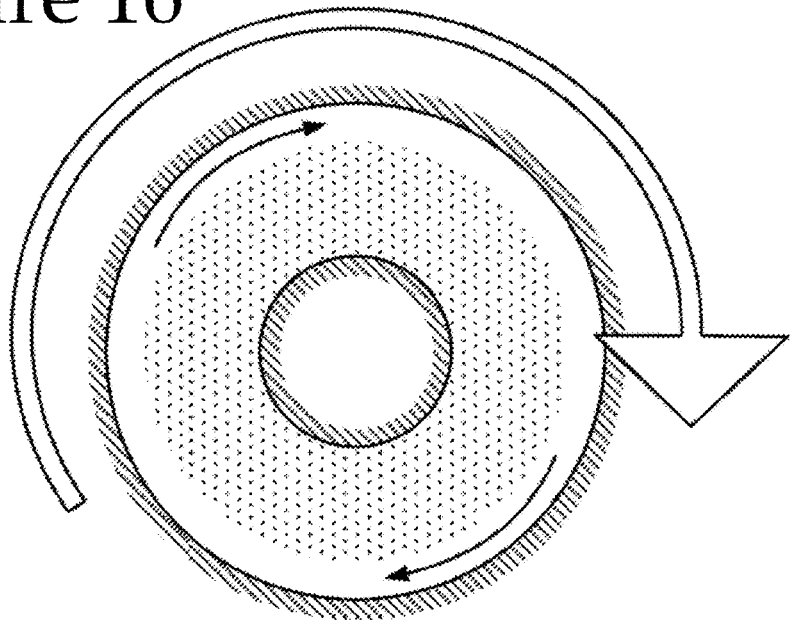
FIG. 16 illustrates a device with a recirculating flow field.
Figure 17:
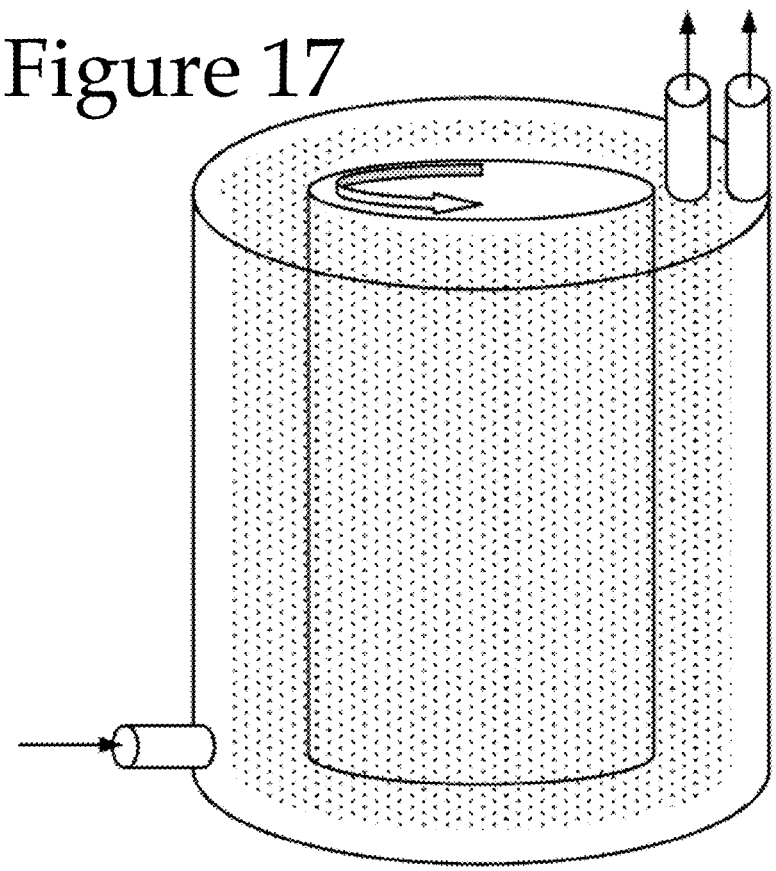
FIG. 17 illustrates a recirculating flow field with flow driven by the inner rotating cylinder.

Depending on the objective of the process, the particle depleted or particle rich effluent may be re-circulated. Devices may also be created with re-circulating flow fields. FIG. 16 illustrates re-circulating of a flow field driven by shear or by using other driving mechanisms such as magnetohydrodynamic pumping available with micro-fluidic devices. As shown, the flow may be driven by movement of an outer solid boundary. Alternate shear driven configurations may be possible including movement of the inner boundary, or by replacing the moving boundary with a fluid path to drive the recirculation flow. FIG. 17 illustrates a recirculating flow field with flow driven by an inner rotating cylinder. Inflow of the solution is at the base and two outflow ports are positioned at the top of the device that provides the particle concentrated and depleted solutions. The length of the obstacle field that the solution is exposed to may be dependent on recirculation flow speed and net flow through the device. Because re-circulating flow fields may be created numerous different ways, the device configurations can be different from those exemplary illustrations in the figures, but still operate on the same basic principle.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

The above disclosed subject matter is to be considered illustrative, and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description. While various embodiments of the invention have been described, it will be apparent to those of ordinary skill in the art that many more embodiments and implementations are possible within the scope of the invention. Accordingly, the invention is not to be restricted except in light of the attached claims and their equivalents.

The invention claimed is:

1. A device for interacting with particles in a fluid, the device comprising:
    an inner lumen; and
    a plurality of obstacles disposed in at least a portion of the inner lumen, wherein the obstacles are arranged to separate particles flowing through the device, wherein at least a portion of the individual obstacles each have an asymmetrical property that causes at least some of the particles in the fluid to shift asymmetrically about the individual obstacles with the asymmetrical properties, wherein the asymmetrical properties are oriented and aligned for the separation of the particles flowing through the device.

2. The device of claim 1, wherein the asymmetrical properties result in different magnitudes of particle shift on either side of an asymmetrical obstacle.

3. The device of claim 1, wherein the asymmetrical properties comprise at least one of geometrical shape, surface properties, electrical charge properties, or magnetic properties of the obstacles.

4. The device of claim 3, wherein the asymmetrical surface properties are a result of variation in the binding, affinity or attraction of antibodies, antigens, proteins, or surface molecules.

5. The device of claim 1, wherein the inner lumen is part of a conduit with at least one inlet and at least one outlet.

6. The device of claim 1, wherein the separation creates a concentration of particles in one region in the device.

7. The device of claim 1, wherein the separation depletes the particles in another region in the device.

8. The device of claim 1, wherein the separation occurs within the device.

9. The device of claim 1, wherein the separation is for at least one of life science diagnostics, clinical diagnostics, clinical therapeutics, biotechnology analysis, microfluidics, blood components processing, fermentation processes, biotechnology processes or separation of cells.

10. The device of claim 1, wherein the obstacles comprise multiple groups of obstacles and at least one separation is based on one of the multiple groups.

11. A device for interacting with particles in a particle entrained fluid comprising:
at least one region; and
a group of obstacles in the at least one region, wherein at least a portion of the obstacles in the region each have asymmetrical properties that cause at least some particles from the particle entrained fluid to shift asymmetrically about an individual obstacle resulting in a concentration of particles within at least one portion of the region, further wherein the concentration occurs within the device.

12. The device of claim 11, wherein the concentration of particles is for at least one of life science diagnostics, clinical diagnostics, clinical therapeutics, biotechnology analysis, microfluidics, blood components processing, fermentation processes, biotechnology processes, or separation of cells.

13. The device of claim 11, wherein at least a portion of the concentrated particles are treated, processed, or analyzed within the device.

14. The device of claim 11, wherein the at least one group of obstacles result in a separation or depletion of particles in at least one area of the at least one region.

15. The device of claim 14, wherein at least a portion of the fluid from which at least some particles have been depleted is processed, treated or analyzed within the device.

16. The device of claim 11, wherein the asymmetrical properties cause asymmetrical interactions with the obstacles, and further wherein the asymmetrical properties comprise at least one of geometrical shape, surface properties, electrical charge properties, or magnetic properties of the obstacles in the group of obstacles.

17. A device comprising:
a fluid including a plurality of particles entrained in the fluid, and
a plurality of obstacles in a path of the fluid, wherein at least a portion of the individual obstacles each have an asymmetrical property that cause at least some of the particles to shift asymmetrically about an individual obstacle and that cause at least some of the particles to shift symmetrically about an individual obstacle.

18. The device of claim 17, wherein the asymmetrical properties cause asymmetrical interactions with the obstacles, and further wherein the asymmetrical properties comprise at least one of geometrical shape, surface properties, electrical charge properties, or magnetic properties of the obstacles.

19. The device of claim 17, wherein at least some individual obstacles cause an asymmetrical particle shift with some particles and a symmetrical particle shift with other particles.

20. The device of claim 17, wherein the asymmetrical properties of the obstacles are arranged and aligned such that a net separation from the asymmetrical particle shifts is in a different direction than the net separation that the symmetric sifts.

21. The device of claim 17, wherein the obstacles are arranged and aligned such that a net separation from the asymmetrical particle shifts is in the same direction as the net separation from the symmetric sifts.

* * * * *